United States Patent
Lin et al.

(10) Patent No.: US 12,210,023 B2
(45) Date of Patent: Jan. 28, 2025

(54) α-SYNUCLEIN SENSING FILM, MANUFACTURING METHOD AND USE THEREOF

(71) Applicant: NATIONAL UNIVERSITY OF KAOHSIUNG, Kaohsiung (TW)

(72) Inventors: Hung-Yin Lin, Kaohsiung (TW); Shyh-Chyang Luo, Kaohsiung (TW); Mei-Hwa Lee, Kaohsiung (TW); Zi-Lin Su, Kaohsiung (TW)

(73) Assignee: National University of Kaohsiung, Kaohsiung (TW)

( * ) Notice: Subject to any disclaimer, the term of this patent is extended or adjusted under 35 U.S.C. 154(b) by 792 days.

(21) Appl. No.: 17/328,330

(22) Filed: May 24, 2021

(65) Prior Publication Data
US 2021/0382072 A1    Dec. 9, 2021

(30) Foreign Application Priority Data

Jun. 4, 2020 (TW) ................. 109118820

(51) Int. Cl.
*G01N 33/68* (2006.01)
*G01N 33/487* (2006.01)

(52) U.S. Cl.
CPC ... *G01N 33/6896* (2013.01); *G01N 33/48721* (2013.01); *G01N 2333/4703* (2013.01); *G01N 2600/00* (2013.01)

(58) Field of Classification Search
CPC ......... G01N 33/6896; G01N 33/48721; G01N 2333/4703; G01N 2600/00
See application file for complete search history.

(56) References Cited

U.S. PATENT DOCUMENTS

2018/0095067 A1* 4/2018 Huff ................. G01N 33/48721

FOREIGN PATENT DOCUMENTS

| CN | 109001452 A | 12/2018 |
| CN | 109180812 A | 1/2019 |

OTHER PUBLICATIONS

Erdossy, Julia, Electrosynthesized molecularly imprinted polymers for protein recognition, 2016, Trends in Analytical Chemistry, 79, pp. 179-190 (Year: 2016).*

* cited by examiner

*Primary Examiner* — Jill A Warden
*Assistant Examiner* — Alex Ramirez
(74) *Attorney, Agent, or Firm* — Rosenberg, Klein & Lee

(57) ABSTRACT

The present invention discloses an α-synuclein sensing film, a manufacturing method and a use thereof. The α-synuclein sensing film comprises a base plate and plural α-synuclein sensing polymers polymerized on the base plate. Each of the plural α-synuclein sensing polymers has plural α-synuclein detection holes on a surface thereof. The plural α-synuclein sensing polymers are manufactured by electropolymerization, and the plural α-synuclein detection holes are imprinted by an α-synuclein peptide. A sample to be tested can be applied to the α-synuclein sensing film for detecting the α-synuclein therein.

4 Claims, 18 Drawing Sheets
(4 of 18 Drawing Sheet(s) Filed in Color)
Specification includes a Sequence Listing.

α-SYNUCLEIN SENSING FILM, MANUFACTURING METHOD AND USE THEREOF

BACKGROUND OF THE INVENTION

1. Field of the Invention

The present invention relates to an α-synuclein sensing film, a manufacturing method and a use thereof in which the α-synuclein sensing film is manufactured by imprinting α-synuclein on a high molecular weight polymer and is used to detect α-synuclein in a sample to be tested.

2. Description of Related Art

Alpha-synuclein (α-synuclein) is highly expressed in human brain tissue and is mainly localized at a tip of a neuron cell. It is believed that α-synuclein regulates release of dopamine. An unmutated α-synuclein is soluble, but mutated α-synuclein accumulates in the neuron cells and cannot be removed, which causes a lot of neuron cells to die. Therefore, functions of the brain tissue are affected by the mutated α-synuclein, and α-synuclein is considered to be involved in many kinds of neuron degenerative diseases including Parkinson's disease, dementia with Lewy bodies and multiple system atrophy.

A traditional method to detect α-synuclein in a serum sample or a plasma sample mainly utilizes α-synuclein antibody. For instance, the China Pat. No. CN109001452 (A), issued on 14 Dec. 2018, disclosed an α-synuclein detection probe which comprises a magnetic carrier and a monoclonal α-synuclein antibody connected to a surface of the magnetic carrier, and the α-synuclein detection probe can be used for detecting Parkinson's disease. The China Pat. No. CN109180812(A), issued on 11 Jan. 2019, disclosed an α-synuclein antibody which binds to amino acid residues 118 to 126 of α-synuclein for diagnosing diseases related to α-synuclein. However, the screening and preparation of antibodies are difficult and the method of detecting α-synuclein by using antibody takes a lot of time, so the traditional method is inconvenient to use and costly.

SUMMARY OF THE INVENTION

The present invention relates to an α-synuclein sensing film, a manufacturing method and a use thereof. The α-synuclein sensing film is manufactured by imprinting an α-synuclein peptide on a high molecular weight polymer to obtain the α-synuclein sensing film for detecting α-synuclein in a sample to be tested.

The α-synuclein sensing film comprises a base plate and plural α-synuclein sensing polymers polymerized on the base plate, and each of the plural α-synuclein sensing polymers has plural α-synuclein detection holes thereon.

The present invention also discloses a method for manufacturing an α-synuclein sensing film which comprises the steps of: mixing an α-synuclein peptide with a monomer material for a high molecular weight polymer to obtain a mixture, and polymerizing the mixture on a base plate by electropolymerization to form plural α-synuclein sensing polymer thereon. An amino acid sequence of the α-synuclein peptide of the present invention is selected from a group consisting of SEQ ID NO:1, SEQ ID NO:2, SEQ ID NO:3 and SEQ ID NO:4.

The present invention also discloses a method for detecting α-synuclein which comprises applying a sample to be tested to an α-synuclein sensing film to detect α-synuclein in the sample. The α-synuclein sensing film comprises a base plate and plural α-synuclein sensing polymers polymerized on the base plate, and each of the plural α-synuclein sensing polymers has plural α-synuclein detection holes on a surface thereof.

In an embodiment of the present invention, the base plate is a conductive base plate and the α-synuclein sensing polymers are high molecular weight polymers imprinted by an α-synuclein peptide.

In an embodiment of the present invention, the conductive base plate is at least one of an indium tin oxide (ITO) base plate, a polyethylene terephthalate (PET) flexible conductive glass plate, an aluminum-doped zinc oxide (AZO) conductive base plate, a fluorine doped tin oxide (FTO) conductive base plate and a silicon dioxide conductive base plate, the high molecular weight polymer is polymerized by a monomer material comprising 3,4-ethylenefioxythiophene (EDOT), hydroxymethyl 3,4-ethylenedioxythiophene (EDOT-OH) or a combination thereof.

In an embodiment of the present invention, an amino acid sequence of the α-synuclein peptide is selected from a group consisting of SEQ ID NO:1, SEQ ID NO:2, SEQ ID NO:3 and SEQ ID NO:4 In an embodiment of the present invention, a current density of the α-synuclein sensing film ranges from 0.01 to 500 mA.

In an embodiment of the present invention the sample is selected from a group consisting of a blood sample, an urine sample, a saliva sample, a sweat sample, a tear sample, a cerebrospinal sample or a sample collected from a tissue or an organ of an organism.

Accordingly, the α-synuclein sensing film of the present invention is manufactured by electropolymerization a mixture containing α-synuclein peptide and a monomer material for a high molecular weight polymer on a base plate to obtain an α-synuclein sensing polymer. The α-synuclein sensing polymer specifically recognizes and binds the α-synuclein, and is convenient to use.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18 (B) is an immunofluorescence photograph showing expression of SNCA of midbrain organoids.

DETAILED DESCRIPTION OF THE PREFERRED EMBODIMENT

To provide a thorough understanding of the present invention, an exemplary embodiment of the present invention will be described in detail with reference to the accompanying drawings.

The present invention discloses an α-synuclein sensing film, a manufacturing method and a use thereof. The α-synuclein sensing film comprises a base plate and plural α-synuclein sensing polymers polymerized on the base plate, and each of the plural α-synuclein sensing polymers has plural α-synuclein detection holes thereon. The base plate is a conductive base plate including but not limited to an indium tin oxide (ITO) base plate, a polyethylene terephthalate (PET) flexible conductive glass plate, an aluminum-doped zinc oxide (AZO) conductive base plate, a fluorine doped tin oxide (FTO) conductive base plate and a silicon dioxide conductive base plate. The plural α-synuclein sensing polymers are high molecular weight polymers imprinted by an α-synuclein peptide, and the high molecular weight polymers are electropolymerized by 3,4-ethylenefioxythiophene (EDOT), hydroxymethyl 3,4-ethylenedioxythiophene (EDOT-OH) or a combination thereof. The α-synuclein peptide has an amino sequence selected from a group consisting of SEQ ID NO:1 SEQ ID NO:2 SEQ ID NO:3 and SEQ ID NO:4. The α-synuclein sensing film is applied for detecting α-synuclein in a sample to be tested.

Figure 1:
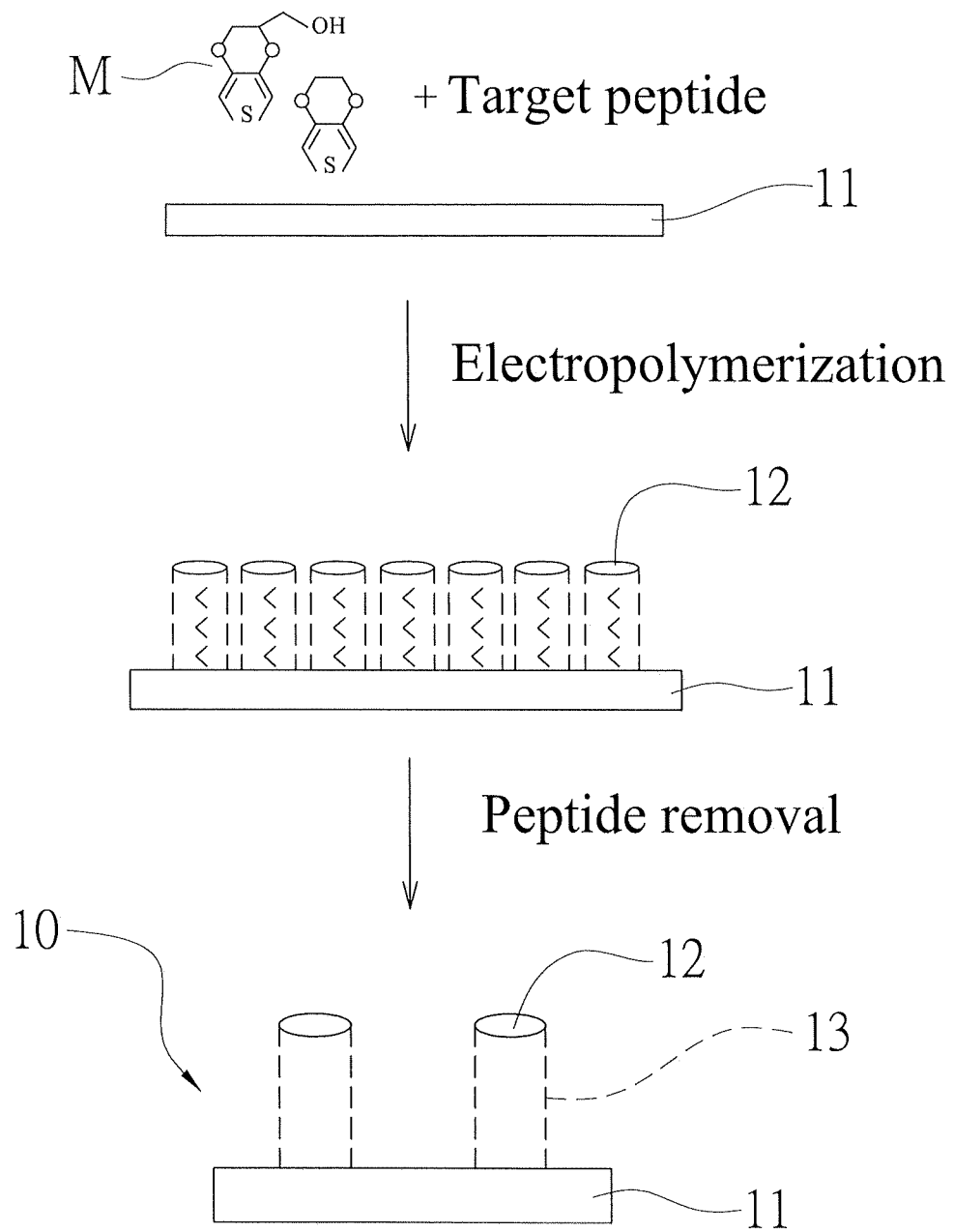
FIG. 1 is a schematic diagram showing a method for manufacturing an α-synuclein sensing film of the present invention.

Referring to FIG. 1, an α-synuclein sensing film 10 of the present invention is manufactured by the steps of mixing an a-synuclein peptide (identified as "target peptide" in FIG. 1) with a monomer material M as EDOT or EDOT-OH to obtain a mixture, polymerizing the mixture on a base plate 11 by electropolymerization to form plural α-synuclein sensing polymer 12 thereon, and removing the a-synuclein peptide to obtain the α-synuclein sensing film 10.

I. Manufacturing of an α-Synuclein Sensing Film

A conductive ITO base plate is cleaned sequentially by deionized water, isopropanol and ethanol, and is dried.

Then, a poly(EDOT-OH) thin film is deposited on the conductive ITO base plate by cyclic volammetry to obtain a pre-deposited ITO base plate. The poly(EDOT-OH) thin film is deposited on the conductive ITO base plate from an aqueous solution containing 10 mM EDOT-OH, 100 mM $LiClO_4$ and 50 mM sodium dodecyl sulfate (SDS) by applying a cyclic potential of −0.6 V to 1.1 V at a scan rate of 100 mV/sec for less than three cycles in which the conductive ITO base plate is used as a working electrode and a silver (Ag)/silver chloride (AgCl) material is used as a reference electrode. The poly(EDOT-OH) thin film on the pre-deposited ITO base plate enhances adhesion of a polymer to the conductive ITO base plate in a following electropolymerization process.

An EDOT monomer material, an EDOT-OH monomer material and an mixture comprising an equal molar amount of EDOT and EDOT-OH are respectively dissolved in a methylene chloride ($CH_2Cl_2$) solvent containing 100 mM tetrabutylammonium perchlorate (TBAP), to obtain a 10 mM EDOT solution, a 10 mM EDOT-OH solution and a mixing solution containing 10 mM EDOT/EDOT-OH mixture. An electrode is placed in a solution at 0° C. for 3 minutes before performing an electropolymerization process. The electropolymerization process is performed at a constant voltage (1.1 V vs $Ag/Ag^+$) for 10 seconds to obtain a polymer deposited base plate in which the polymer is poly-EDOT, poly(EDOT-OH) or poly(EDOT/EDOT-OH) and has micro-nano structure.

To manufacture a peptide-imprinted polymer, an α-synuclein peptide is dissolved in deionized water to obtain a first α-synuclein solution. The EDOT solution, the EDOT-OH solution and the mixing solution described above are respectively mixed with the first α-synuclein peptides solution to obtain a second α-synuclein peptide solution, and the second α-synuclein peptide solution contains 0.01 mg/mL of the α-synuclein peptide.

The α-synuclein peptide used in the present invention comprises Peptide 1, Peptide 2, Peptide 3 and Peptide 4 and the amino acid sequence of the Peptide 1, the Peptide 2, the Peptide 3, and the Peptide 4 are SEQ ID NO:1, SEQ ID NO:2, SEQ ID NO:3, and SEQ ID NO:4 in the sequence listing respectively.

Then, the second α-synuclein peptide solution is used as an electrolyte and the pre-deposited ITO base plate is used as a working electrode to perform an electropolymerization process and form plural α-synuclein sensing polymers on the pre-deposited ITO base plate. In this embodiment, a platinum electrode is used as a counter electrode and a silver (Ag)/silver chloride (AgCl) material is used as a reference electrode. The electropolymerization process is performed at a constant voltage (1.1 V vs Ag/Ag$^+$). After electropolymerization, the pre-deposited ITO base plate is sequentially washed by deionized water, 5 (v/v) % ethanol twice to remove unpolymerized monomer materials and the α-synuclein peptide to obtain the α-synuclein sensing film of the present invention. The α-synuclein sensing film is named MIPs in the following description. As shown in FIG. 1, the α-synuclein sensing film 10 has plural a-synuclein sensing polymers 12 thereon, and each of the plural a-synuclein sensing polymers 12 has plural α-synuclein detection holes 13 on a surface thereof. In addition, a non-imprinted sensing film is manufactured by electropolymerization of the EDOT solution, the EDOT-OH solution or the mixing solution without adding the α-synuclein peptides. The non-imprinted sensing film is considered as a control group and named as NIPs in the following description.

In addition, the MIPs manufactured by a specific monomer material and a specific α-synuclein peptide is named as "MIPs monomer material_peptide". For example, the "MIPs_EDOT_Peptide 1" is an α-synuclein sensing film manufactured by Peptide 1-imprinted poly-EDOT on the conductive base plate, and so on.

An 1 cm$^2$ of the α-synuclein sensing film of the present invention is used as a working electrode and analyzed by a potentiostat. The α-synuclein sensing film of the present invention, a counter electrode and a reference electrode are soaked in an electrolyte containing potassium ferric chloride and potassium ferrocyanide for performing electrochemical analysis by the potentiostat. The counter electrode can be a platinum electrode, a tungsten-molybdenum alloy electrode or a ceramic copper alloy electrode. And the reference electrode can be a Ag/AgCl electrode, a copper-tungsten alloy, a silver-tungsten alloy electrode, a tungsten-molybdenum alloy electrode, or a chrome-copper electrode is used as a reference electrode. In this embodiment, the counter electrode is the platinum electrode and the reference electrode is the Ag/AgCl electrode.

Figure 2A:
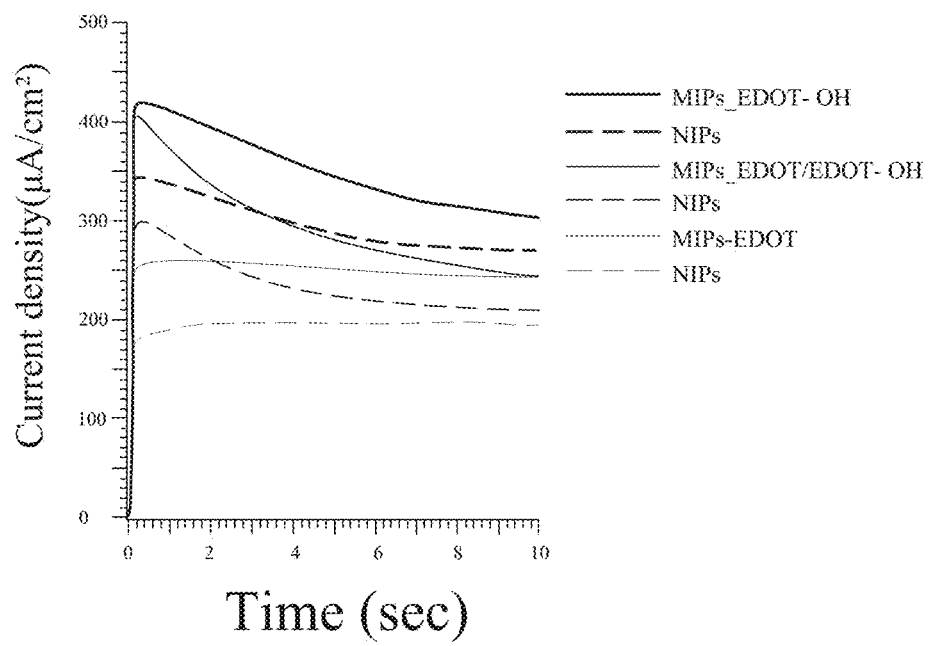
FIG. 2(A) is a line graph showing a current density of an α-synuclein sensing film of the present invention.
Figure 2B:
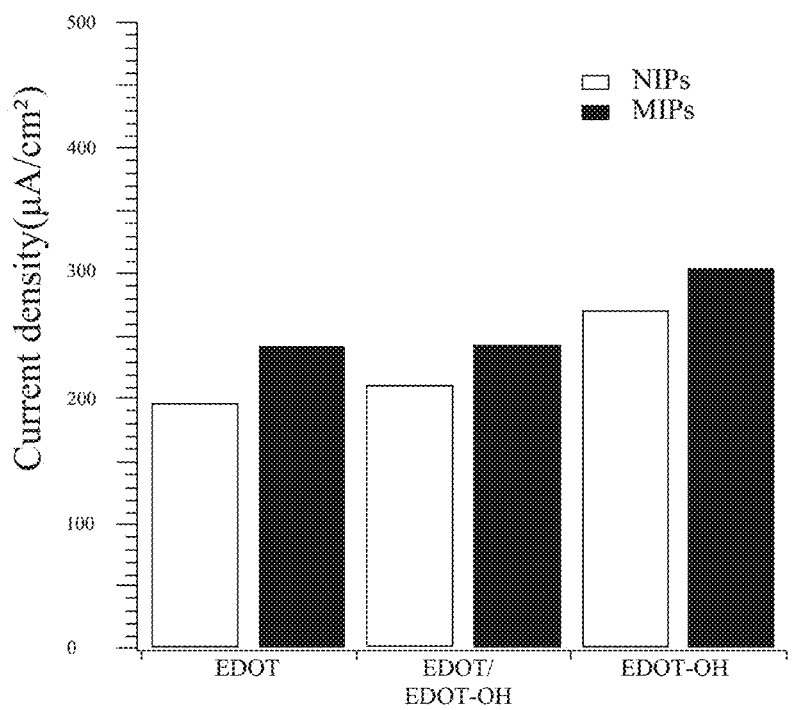
FIG. 2(B) is a bar chart showing a current density of an α-synuclein sensing film of the present invention.

Referring to FIG. 2(A) is a line graph showing current densities of α-synuclein sensing films during electropolymerization under a reaction condition of 1.1 V in which the α-synuclein sensing films are respectively manufactured by different kinds of monomer material accompanied with Peptide 1. According to FIG. 2(A), MIPs_EDOT-OH_Peptide 1 has a highest current density ranging from 350-400 μm/cm$^2$ among the tested α-synuclein sensing films. The MIPs_EDOT_Peptide 1 has a lowest current density ranging from 200-250 μm/cm$^2$. FIG. 2(B) show a current density of the MIPs and the NIPs after charging for 20 seconds. The non-imprinted NIPs_PEDOT has a current density about 50 μm/cm$^2$, which is lower than the current density of the MIPs_PEDOT. In other tested samples, the MIPs imprinted with a peptide has a higher current density than the non-imprinted NIPs manufactured by the same monomer material.

Figure 3A:
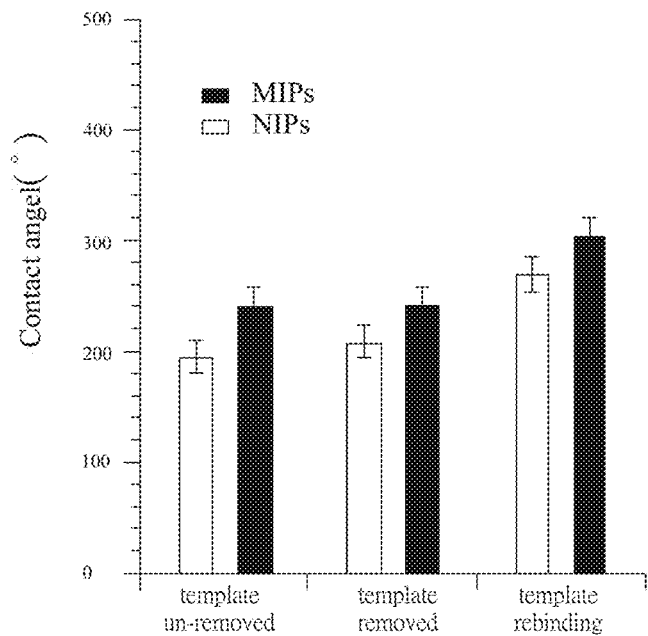
FIG. 3(A) is a bar chart showing a contact angle of an α-synuclein sensing film of the present invention.
Figure 3B:
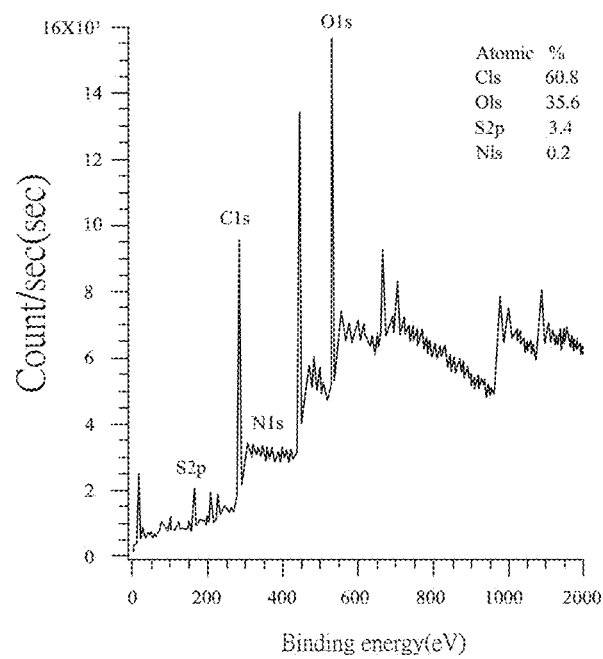
FIG. 3(B) is a line chart showing an electron spectroscopy for chemical analysis result of an α-synuclein sensing film of the present invention.

FIG. 3(A) shows a water contact angle analytic result of the NIPs_EDOT-OH and MIPs_EDOT-OH_Peptide 1 before removing the template, after removing the template and after rebinding to the template. According to FIG. 3(A), the water contact angle of the MIPs_EDOT-OH_Peptide 1 is 54.2±0.6° and the water contact angle of the NIPs_EDOT-OH before removing the template is 35.0±1.1° which is lower than the MIPs_EDOT-OH_Peptide 1. This result indicated that a surface of the MIPs_EDOT-OH_peptide 1 is more hydrophobic than the NIPs_EDOT-OH. After removing the template, the water contact angle of both the NIPs_EDOT-OH and the MIPs_EDOT-OH_Peptide 1 are increased which indicated the hydrophobicity of both NIPs_EDOT-OH and the MIPs_EDOT-OH_Peptide 1 are elevated. Further, after rebinding to Peptide 1, the water contact angle of the NIPs_EDOT-OH and the MIPs_EDOT-OH_Peptide 1 are similar, about 102.9±3.7°. Referring to FIG. 3(B), the MIPs_EDOT-OH_Peptide 1 is analyzed by an electron spectroscopy for chemical analysis (ESCA) after washed by 5 (v/v) % ethanol. FIG. 3(B) indicated that the peptide was removed completely by 5 (v/v) % ethanol.

FIG. 4 shows scanning electron microscopic photographs of the NIPs_EDOT-OH and MIPs EHOT-OH_Peptide 1, the bright areas in the SEM photographs are regions of high scattering, such as rough surfaces. FIG. 4(A) is a photograph of the MIPs_EDOT-OH_Peptide 1 before removing the template, FIG. 4(B) is a photograph of the NIPs_EDOT-OH before removing the template and both of the MIPs_EDOT-OH_Peptide 1 and the NIPs_EDOT-OH has similar tubular structures. It indicated that the presence of the peptide template during electropolymerization does not affect the formation of the poly(EDOT-OH) nanostructures.

Figure 4A:
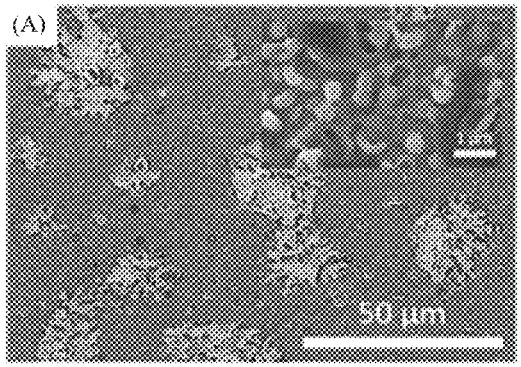
FIG. 4(A)-FIG. 4(F) show scanning electron microscopic photographs of an α-synuclein sensing film of the present invention.
Figure 4B:
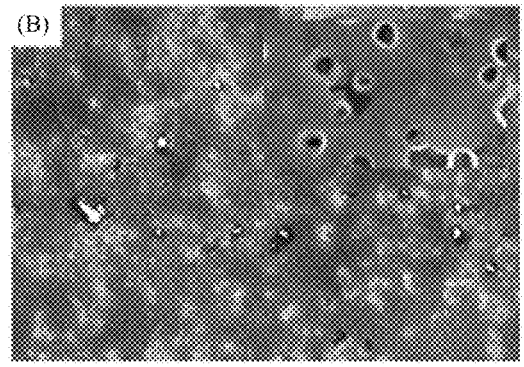
Figure 4C:
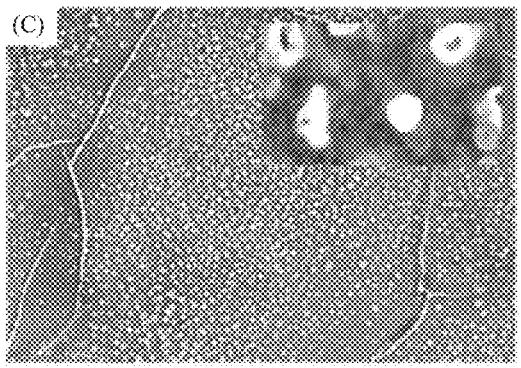
Figure 4D:
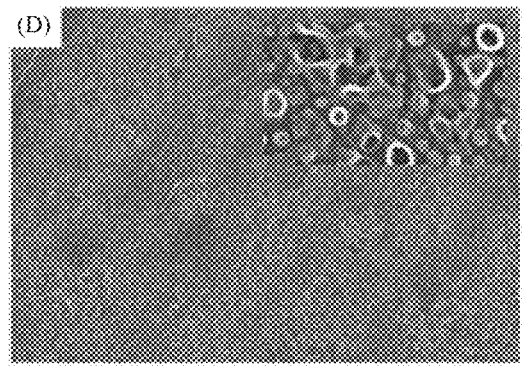
Figure 4E:
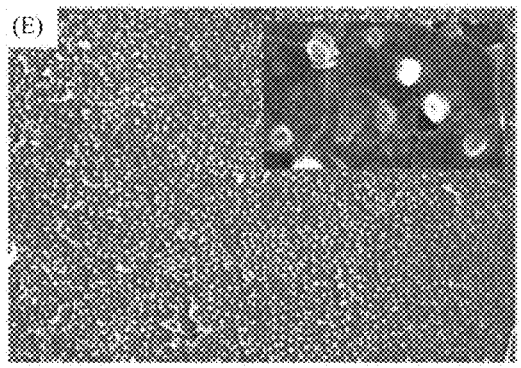
Figure 4F:
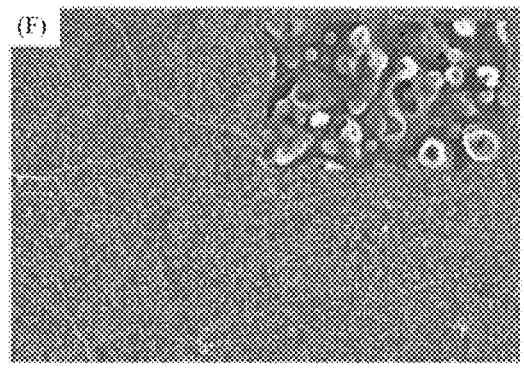
Figure 5A:
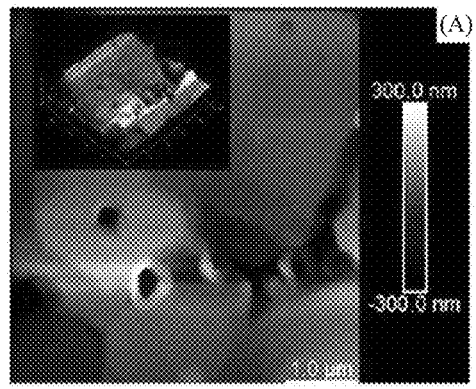
FIG. 5(A)-FIG. 5(F) show atomic force microscopic photographs of an α-synuclein sensing film of the present invention.
Figure 5B:
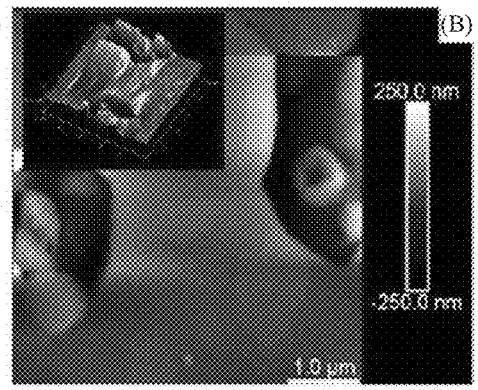
Figure 5C:
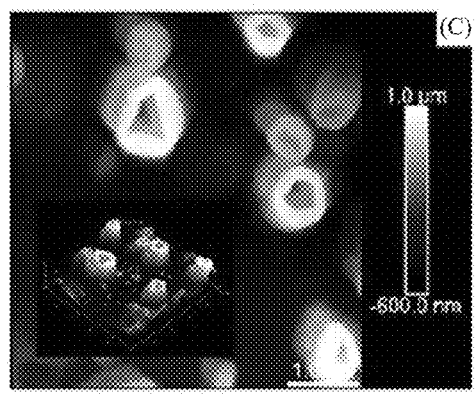
Figure 5D:
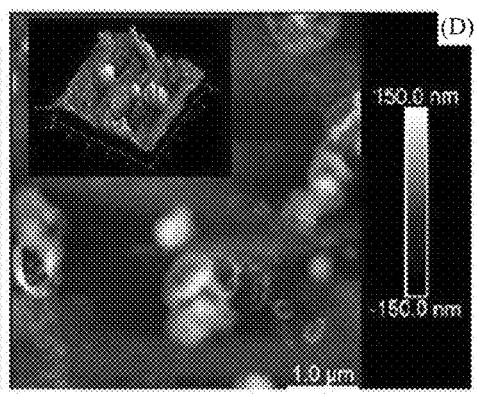
Figure 5E:
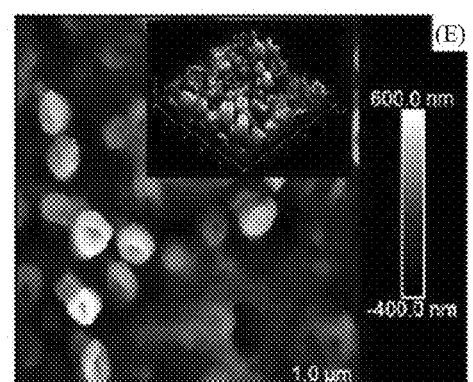
Figure 5F:
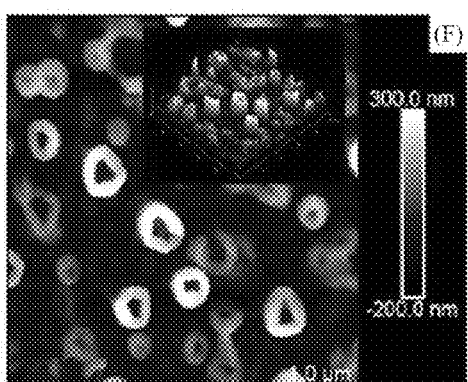

FIG. 4(C) is a photograph of the MIPs_EDOT-OH_Peptide 1 after removing the template, and FIG. 4(D) is a photograph of the NIPs_EDOT-OH after removing the template, both of the MIPs_EDOT-OH_Peptide 1 and NIPs_EDOT-OH have similar tubular structures. FIG. 4(E) is a photograph of the MIPs_EDOT-OH_Peptide 1 after re-binding with 0.65 nM (1 ng/mL) Peptide 1, and FIG. 4(F) is a photograph of the NIPs_EDOT-OH after re-binding with 0.65 nM (1 ng/mL) Peptide 1, and both of the MIPs_EDOT-OH_Peptide 1 and NIPs_EDOT-OH have similar tubular structures.

FIG. 5 shows atomic force microscopic (AFM) photographs of the NIPs_EDOT-OH and the MIPs_EDOT-OH Pwptide 1. FIG. 5(A) is the MIPs_EDOT-OH_Peptide 1 before removing the template, FIG. 5(B) is the NIPs_EDOT-OH before removing the template, FIG. 5(C) is the MIPs_EDOT-OH_Peptide 1 after removing the template, FIG. 5(D) is the NIPs_EDOT-OH after removing the template, FIG. 5(E) is the MIPs_EDOT-OH_Peptide 1 re-binding with 0.65 nM (1 ng/mL) Peptide 1, and FIG. 5(F) is a photograph of the NIPs_EDOT-OH after re-binding with 0.65 nM (1 ng/mL) Peptide 1. Tubular structures are also observed in all the photographs in the FIG. 5 which indicated that the presence of the peptide templates does not affect the formation of the poly(EDOT-OH) nanostructure.

The MIPs are then analyzed by cyclic voltammetry to calculate imprinting efficiency of the MIPs under a scanning voltage of −0.85~0.8 V, a scan rate of 0.1 V/sec. The equation to calculate imprinting efficiency is:

$$\text{Imprinting efficiency}(\alpha) = \text{current of the MIPs/current of the NIPs}$$

Figure 6A:
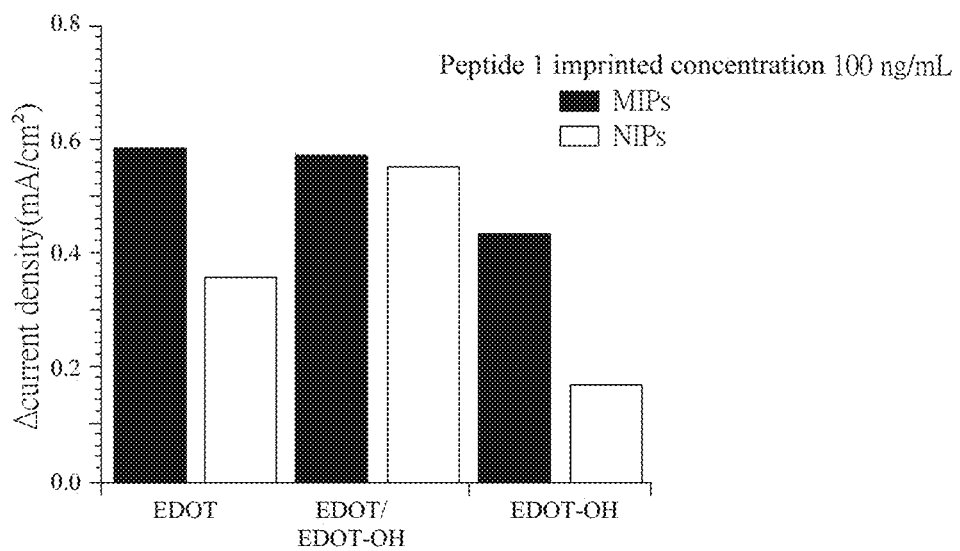
FIG. 6 (A) is a bar chart showing a current density differences of an α-synuclein sensing film imprinted by a first α-synuclein peptide of the present invention.
FIG. 6(B) is a bar chart showing a current density differences of an α-synuclein sensing film imprinted by a second α-synuclein peptide of the present invention.

Referring to FIG. 6(A), current density differences (Δcurrent density) of Peptide 1-imprinted MIPs are disclosed. The current density differences of the MIPs_EDOT_Peptide 1 is 0.586 mA/cm$^2$, and the current density differences of the NIPs_EDOT is 0.361 mA/cm$^2$. The current density differences of the MIPs_EDOT/EDOT-OH_Peptide 1 is 0.572 mA/cm$^2$, and the current density differences of the NIPs_EDOT/EDOT-OH is 0.552 mA/cm$^2$. The current density differences of the MIPs_EDOT-OH_Peptide 1 is 0.439 mA/cm$^2$, and the current density of the NIPs_EDOT-OH is 0.173 mA/cm$^2$. In addition, the imprinting efficiency (α) of the MIPs_EDOT_Peptide 1 is 1.623, the imprinting efficiency (α) of the MIPs_EDOT/EDOT-OH_Peptide 1 is 1.036, and the imprinting efficiency (α) of the MIPs_EDOT-OH_Peptide 1 is 2.537. The results indicated that the α-synuclein sensing film manufactured by the EDOT-OH material has a better imprinting efficiency in the Peptide 1-imprinted MIPs.

Figure 6B:
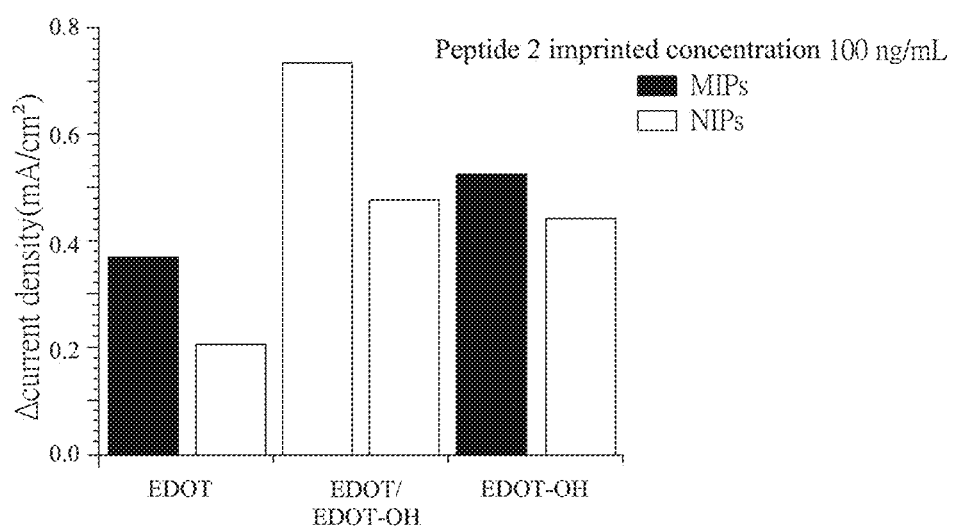

Referring to FIG. 6(B), the current density differences of the MIPs_EDOT_Peptide 2 is 0.369 mA/cm², and the current density differences of the NIPs_EDOT is 0.203 mA/cm². The current density differences of the MIPs_EDOT/EDOT-OH_Peptide 2 is 0.740 mA/cm², and the current density differences of the NIPs_EDOT/EDOT-OH is 0.475 mA/cm². The current density differences of the MIPs_EDOT-OH_Peptide 2 is 0.530 mA/cm², and the current density differences of the NIPs_EDOT-OH is 0.444 mA/cm². In addition, the imprinting efficiency (α) of the MIPs_EDOT_Peptide 2 is 1.82, the imprinting efficiency (α) of the MIPs_EDOT/EDOT-OH_Peptide 2 is 1.56, and the imprinting efficiency (α) of the MIPs_EDOT-OH_Peptide 2 is 1.19. The results indicated that the α-synuclein sensing film manufactured by the EDOT material has a better imprinting efficiency in the Peptide 2-imprinted MIPs.

Figure 7:
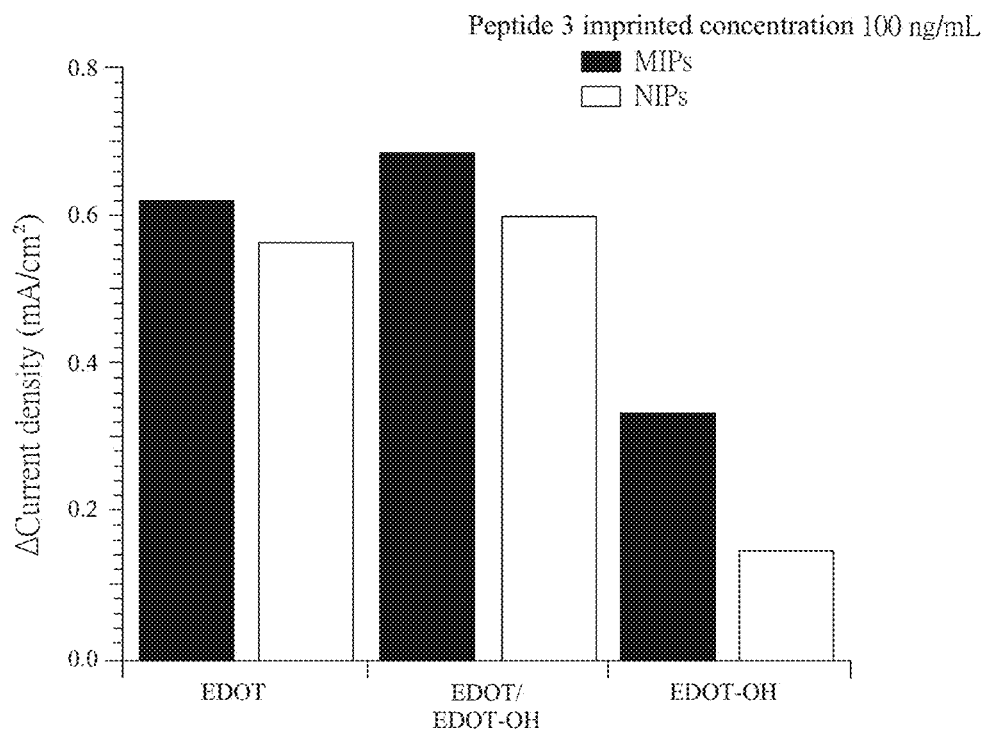
FIG. 7 is a bar chart showing a current density differences of an α-synuclein sensing film imprinted by a third α-synuclein peptide of the present invention.

Referring to FIG. 7, the current density differences of the MIPs_EDOT_Peptide 3 is 0.6205 mA/cm², and the current density differences of the NIPs_EDOT is 0.565 mA/cm². The current density differences of the MIPs_EDOT/EDOT-OH_Peptide 3 is 0.688 mA/cm², and the current density differences of the NIPs_EDOT/EDOT-OH is 0.602 mA/cm². The current density differences of the MIPs_EDOT-OH_Peptide 3 is 0.333 mA/cm², and the current density differences of the NIPs_EDOT-OH is 0.144 mA/cm². In addition, the imprinting efficiency (α) of the MIPs_EDOT_Peptide 3 is 1.10, the imprinting efficiency (α) of the MIPs_EDOT/EDOT-OH_Peptide 3 is 1.14, and the imprinting efficiency (α) of the MIPs_EDOT-OH_Peptide 3 is 2.31. The results indicated that the α-synuclein sensing film manufactured by the EDOT-OH material has a better imprinting efficiency in the Peptide 3-imprinted MIPs.

Figure 8:
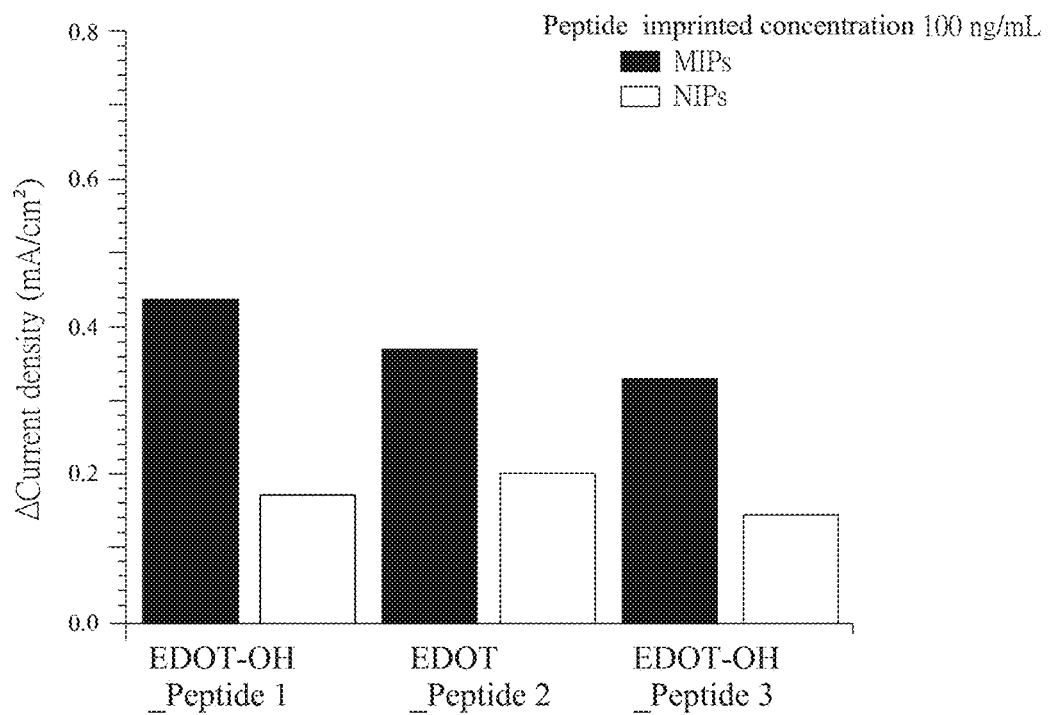
FIG. 8 is a bar chart showing a current density differences of an α-synuclein sensing film imprinted by a first α-synuclein peptide, a second α-synuclein peptide and a third α-synuclein peptide of the present invention.

Referring to FIG. 8, the MIPs_EDOT-OH_Peptide 1, the MIPs_EDOT_Peptide 2 and the MIPs_EDOT-OH_Peptide 3 are analyzed. The current density differences of the MIPs_EDOT_Peptide 1 is 0.439 mA/cm², the current density differences of the NIPs_EDOT-OH is 0.173 mA/cm², and the imprinting efficiency (α) of the MIPs_EDOT-OH_Peptide 1 is 2.54. The current density differences of the MIPs_EDOT_Peptide 2 is 0.369 mA/cm², the current density differences of the NIPs_EDOT is 0.203 mA/cm², and the imprinting efficiency (α) of the MIPs_EDOT_Peptide 2 is 1.82. The current density differences of the MIPs_EDOT-OH_Peptide 3 is 0.333 mA/cm², the current density differences of the NIPs_EDOT-OH is 0.144 mA/cm², and the imprinting efficiency (α) of the MIPs_EDOT-OH_Peptide 3 is 2.31. The results indicated that the α-synuclein sensing film polymerized by EDOT-OH and imprinted by the Peptide 1 has a better imprinting efficiency.

Figure 9:
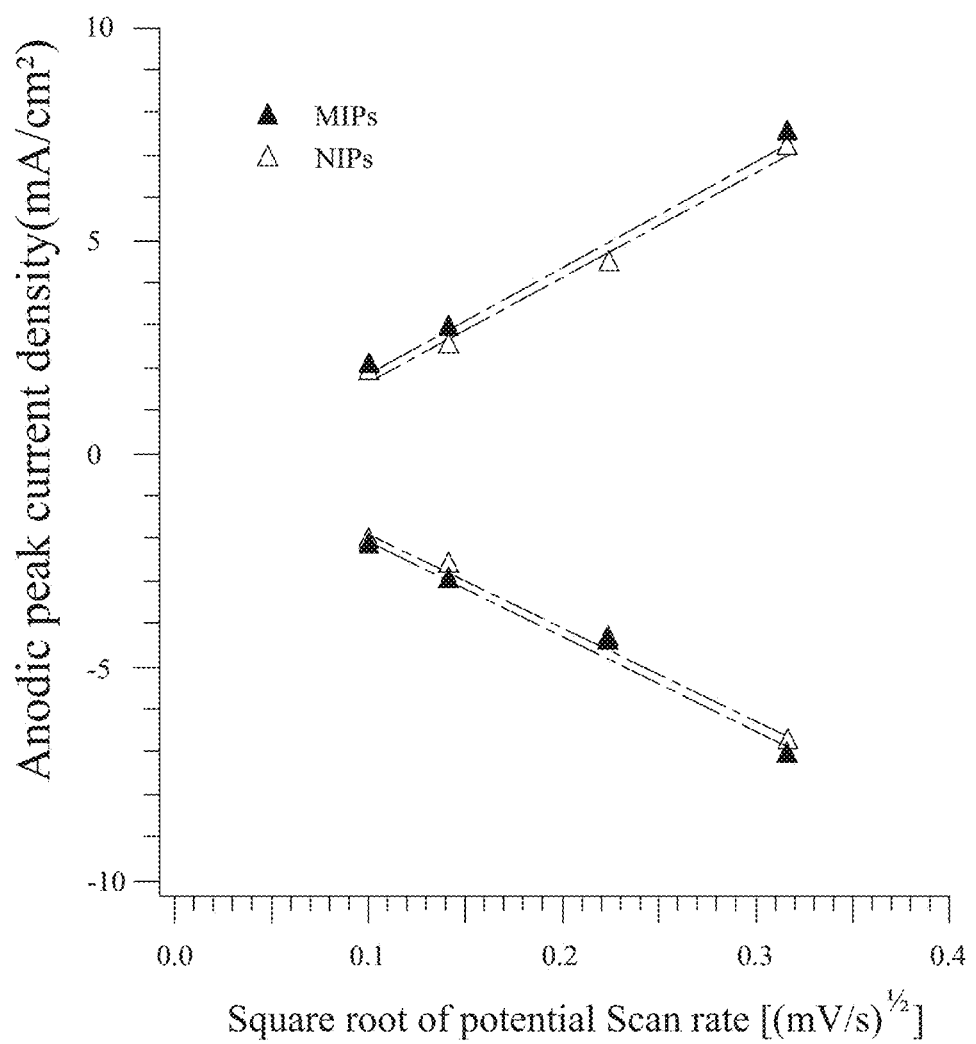
FIG. 9 is a line graph showing a current density against a square root of a scan rate of an α-synuclein sensing film of the present invention.

FIG. 9 shows a current density against a square root of a scan rate of the MIPs_EDOT-OH_Peptide 1 (marked as MIPs in FIG. 9) and NIPs_EDOT-OH (marked as NIPs in FIG. 9) to analyze a linear-relation of a peak current of the MIPs_EDOT-OH_Peptide 1 and the NIPs_EDOT-OH. Furthermore, surface areas of the MIPs_EDOT-OH_Peptide 1 and NIPs_EDOT-OH are calculated by the Randle s-Sevcik equation. The surface area of the MIPs_EDOT-OH_Peptide 1 is 1.746 cm², and the surface area of the NIPs_EDOT-OH is 1.726 cm².

Figure 10:
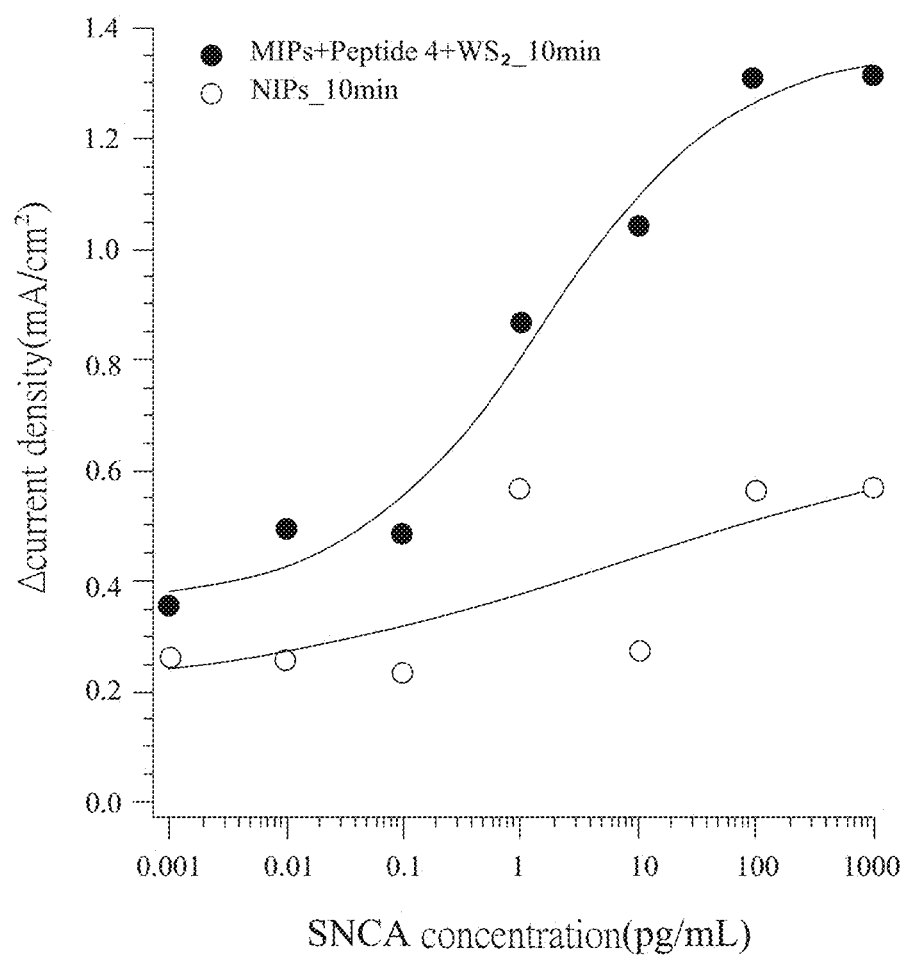
FIG. 10 is a line graph showing a current density of an α-synuclein sensing film imprinted by a fourth α-synuclein peptide and tungsten sulfide in the present invention.

FIG. 10 is a current density differences analyzing result of a NIPs and a MIPs imprinted by 50 μg of the Peptide 4 and tungsten sulfide ($WS_2$). The NIPs and the MIPs in FIG. 10 are interacted with a solution containing 0.001~1000 pg/mL α-synuclein and analyzed to obtain the current density differences thereof. According to FIG. 10, the imprinting efficiency (α) of the MIPs Peptide 4+$WS_2$ is 2.3.

Figure 11A:
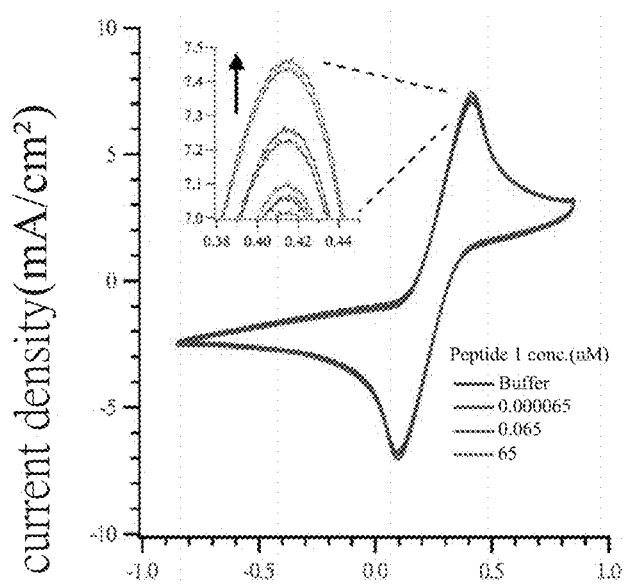
FIG. 11(A) is a line graph showing a cyclic voltammetry curve of an α-synuclein sensing film of the present invention.
Figure 11B:
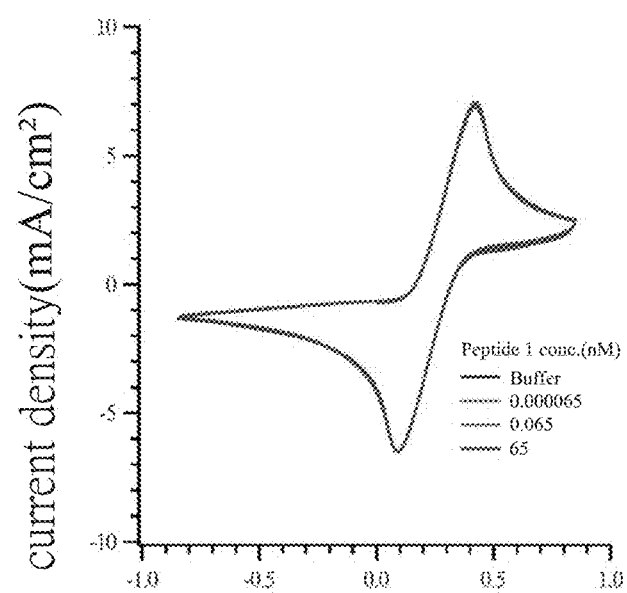
FIG. 11(B) is a line graph showing a cyclic voltammetry curve of an α-synuclein sensing film of the present invention.

FIG. 11(A) shows a cyclic voltammetry analyzing result of the MIPs_EDOT-OH_Peptide 1 interacting with a solution containing 0.000065 nM-65 nM (0.1 zg/mL-0.1 ng/mL) of the Peptide 1, and FIG. 11(B) shows a cyclic voltammetry analyzing result of the NIPs_EDOT-OH interacting with a solution containing 0.000065 nM-65 nM (0.1 zg/mL~0.1 ng/mL) of the Peptide 1. The oxidation peak of the MIPs_EDOT-OH_Peptide 1 ranges from 410-420 mV, and the reduction voltage ranges from 90-100 mV. According to FIG. 11(A), before interacting to the Peptide 1, the peak anodic current density of the MIPs_EDOT-OH_Peptide 1 is 7.4 mA/cm². After interacting with the Peptide 1, the peak anodic current density of the MIPs_EDOT-OH_Peptide 1 is increased gradually. Referring to FIG. 11(B), before interacting to the Peptide 1, the peak anodic current density of the NIPs_EDOT-OH is 6.9 mA/cm². After interacting with the 0.65 nM (1.0 ng·mL$^{-1}$) Peptide 1, the peak anodic current density of the NIPs_EDOT-OH is increased to 7.1 mA/cm².

Figure 12A:
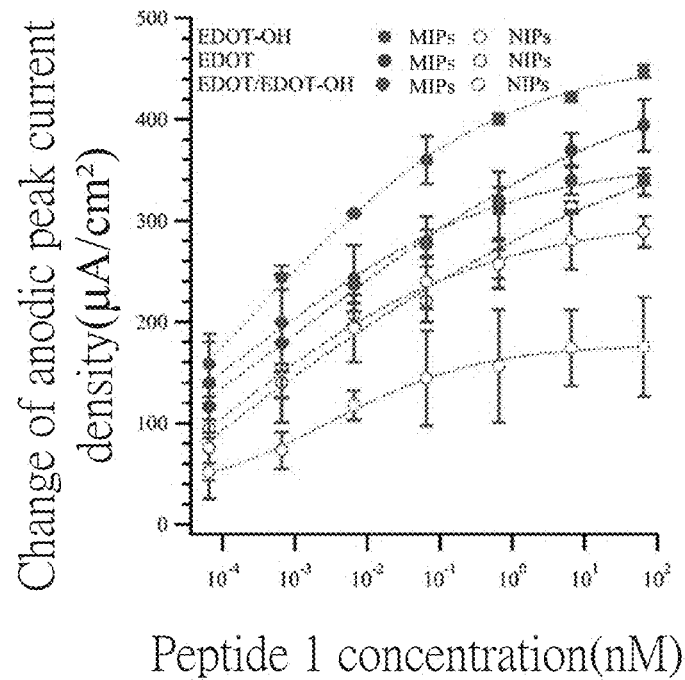
FIG. 12(A) is a line graph showing an anodic peak current density of α-synuclein sensing films of the present invention.
Figure 12B:
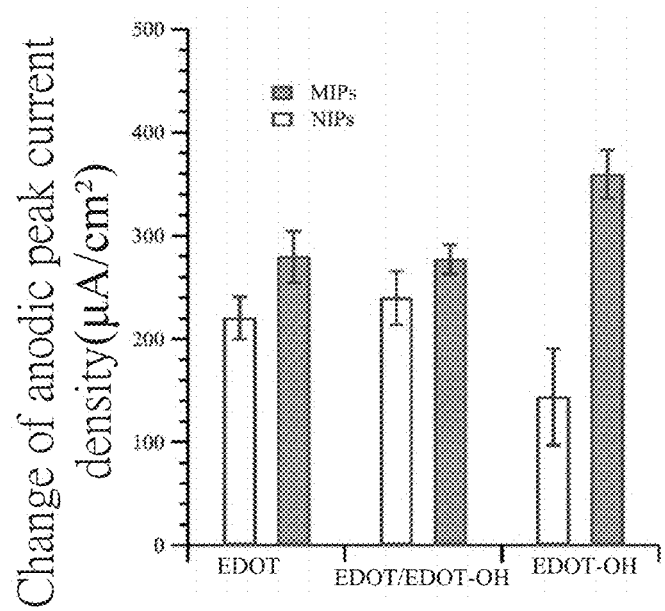
FIG. 12 (B) is a bart chart showing an anodic peak current density of α-synuclein sensing films of the present invention.

FIG. 12 (A) shows anodic peak current density of the α-synuclein sensing films manufactured by Peptide 1-imprinted polymers. The Peptide 1-imprinted α-synuclein sensing films are interacted with different amount of the Peptide 1 and analyzed by cyclic voltammetry. The anodic peak current density of the Peptide 1-imprinted MIPs are higher than the anodic peak current density of the NIPs. In addition, the anodic peak current density of the Peptide 1-imprinted MIPs is increased along with interacting with the Peptide 1 having a higher concentration, which indicated the α-synuclein sensing film of the present invention can detect α-synuclein. Further, the anodic peak current density of the MIPs_EDOT-OH-Peptide 1 and the NIPs_EDOT-OH has a largest difference. Referring to FIG. 12(B), a bart chart showing an anodic peak current density of non-imprinted sensing films (NIPs) and Peptide-1 imprinted α-synuclein sensing films (MIPs) is disclosed. After interacting to 0.65 nM Peptide 1, the MIPs_EDOT-OH_Peptide 1 has a highest current density, the MIPs_EDOT_Peptide 1 has a lowest density, and the MIPs_EDOT/EDOT-OH_Peptide 1 has an intermediate current density. Among the non-imprinted sensing films, the NIPs_EDOT-OH has a lowest current density, and the current densities of the NIPs_EDOT/EDOT-OH and the NIPs_EDOT are similar.

Figure 13:
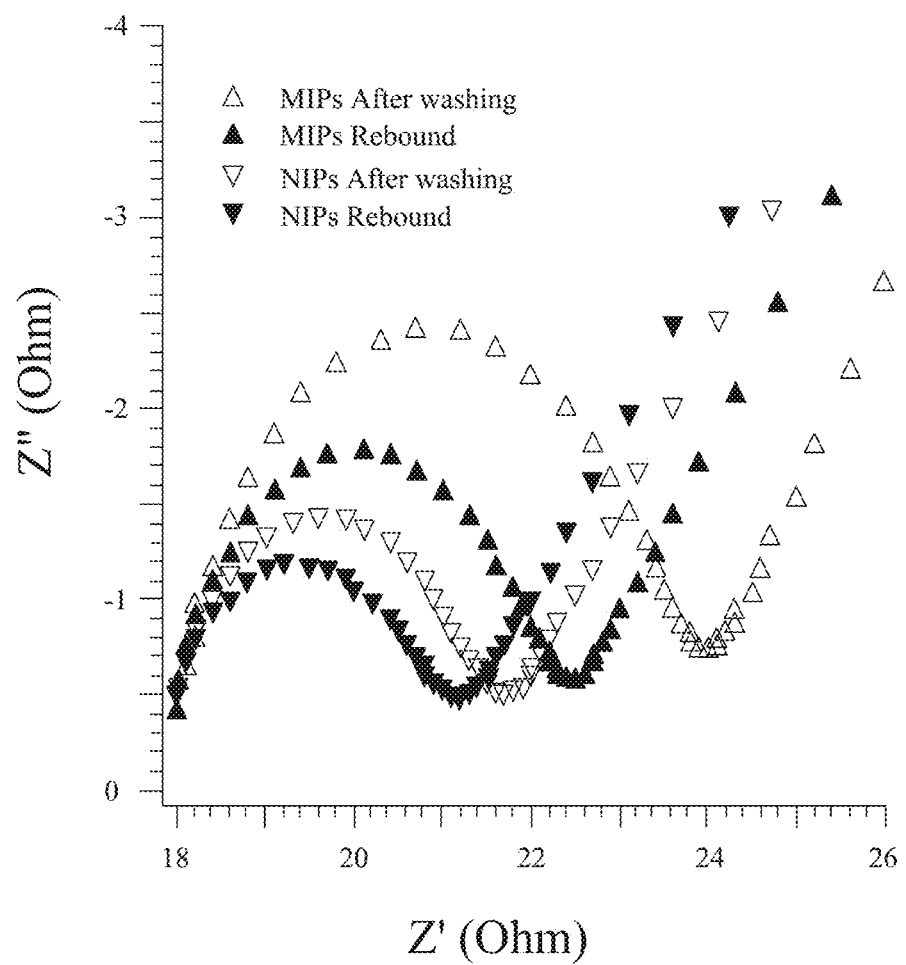
FIG. 13 is a dot diagram showing an AC impedance of an α-synuclein sensing film of the present invention.

FIG. 13 shows a Nyquist plot of the MIPs_EDOT-OH_Peptide 1 and NIPs_EDOT-OH to present an alternative circuit (AC) impedance character thereof. The "After washing" in FIG. 13 indicates that the template is removed from MIPs or a washed NIPs after electropolymeriation, and the "Rebound" indicated a MIPs or a NIPs are interacted with the Peptide 1. The AC impedance signals of the NIPs before and after interacting with the Peptide 1 is not significantly different. However, the AC impedance signals of the MIPs after interacting with the Peptide 1 is decreased compared to the MIPs before interacting with the Peptide 1.

Figure 14:
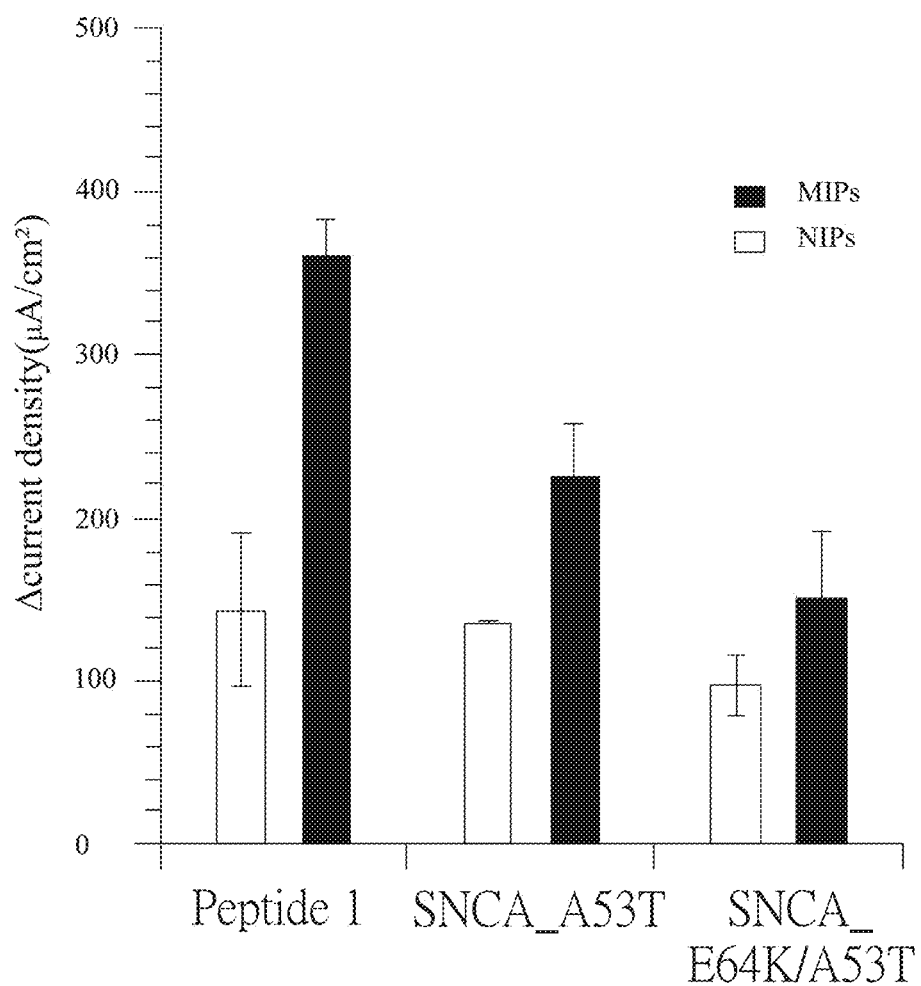
FIG. 14 is a bar chart showing a current density of an α-synuclein sensing film of the present invention when binding to α-synuclein.

FIG. 14 shows a current density analysis of the NIPs_EDOT-OH and the MIPs_EDOT-OH_Peptide 1 interacting to 0.65 nM Peptide 1 and α-synuclein mutant. The SNCA_A53T indicated a substitution of threonine for alanine at the 53$^{th}$ amino acid of α-synuclein, the SNCA E64K indicated a substitution of lysine for the 64$^{th}$ amino acid of α-synuclein, and the SNCA E64K/A53T indicated a double substitution of amino acids at the 53$^{th}$ amino acid and the 64$^{th}$ amino acid of α-synuclein. The Δcurrent densities of the MIPs interacting to the SNCA_A53T and the SNCA E64K/

A53T are decreased compared to the Δcurrent densities of the MIPs interacting to Peptide 1.

Figure 15:
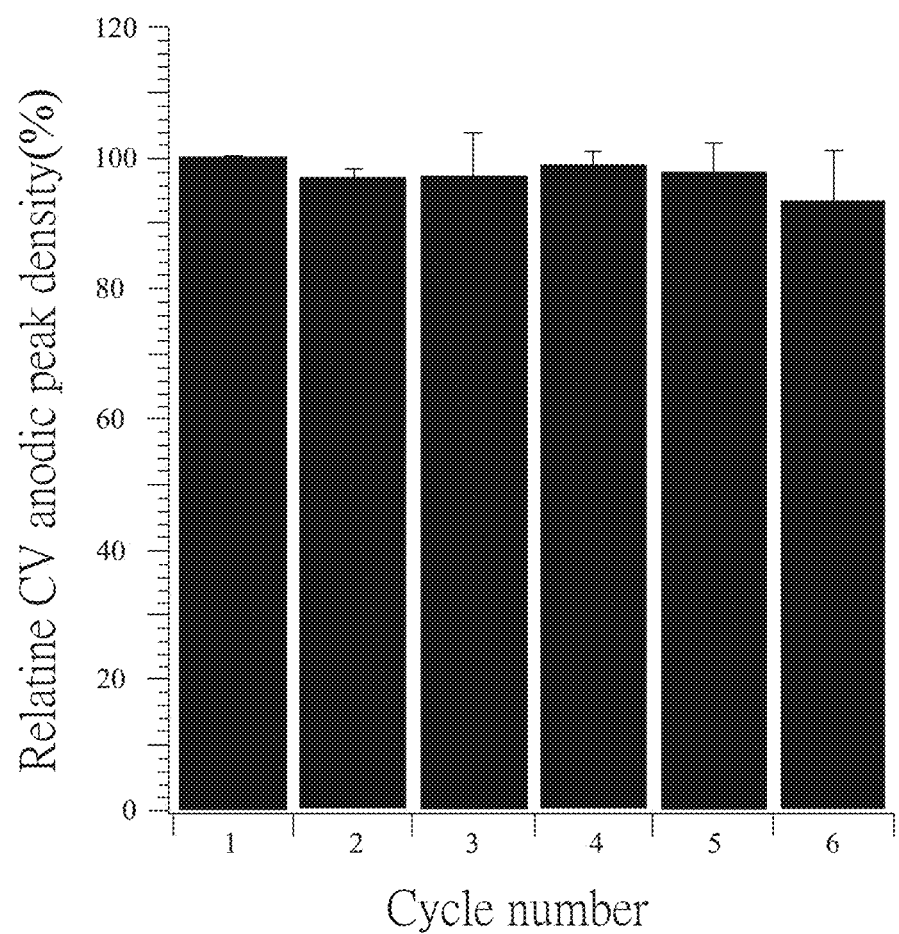
FIG. 15 a bar chart showing a number of repeated uses of an α-synuclein sensing film of the present invention.

FIG. 15 a bar chart showing a number of repeated uses of the MIPs_EDOT-OH_Peptide 1. An 0.65 nM (1 ng/mL) of the Peptide 1 solution is applied to the MIPs_EDOT-OH_Peptide 1, and a current density of the MIPs_EDOT-OH_Peptide 1 is measured to obtain a first measurement result. The MIPs_EDOT-OH_Peptide 1 is then washed by deionized water and dried. Then the same MIPs_EDOT-OH_Peptide 1 is interacted to a fresh Peptide 1 solution, and a current density of the MIPs_EDOT-OH_Peptide 1 is measured to obtain a second measurement result. The measurement steps above are repeated for 6 times to obtain 6 measurement results. The first measurement result is considered as 100% to calculate a relative current of the second to sixth measurement results. Referring to FIG. 15, the six measurement results are similar except that the relative current of the sixth measurement result is decreased slightly. It suggested that α-synuclein sensing film of the present invention is reusable, and the measurement result obtained by the reused α-synuclein sensing film is reliable.

Figure 16:
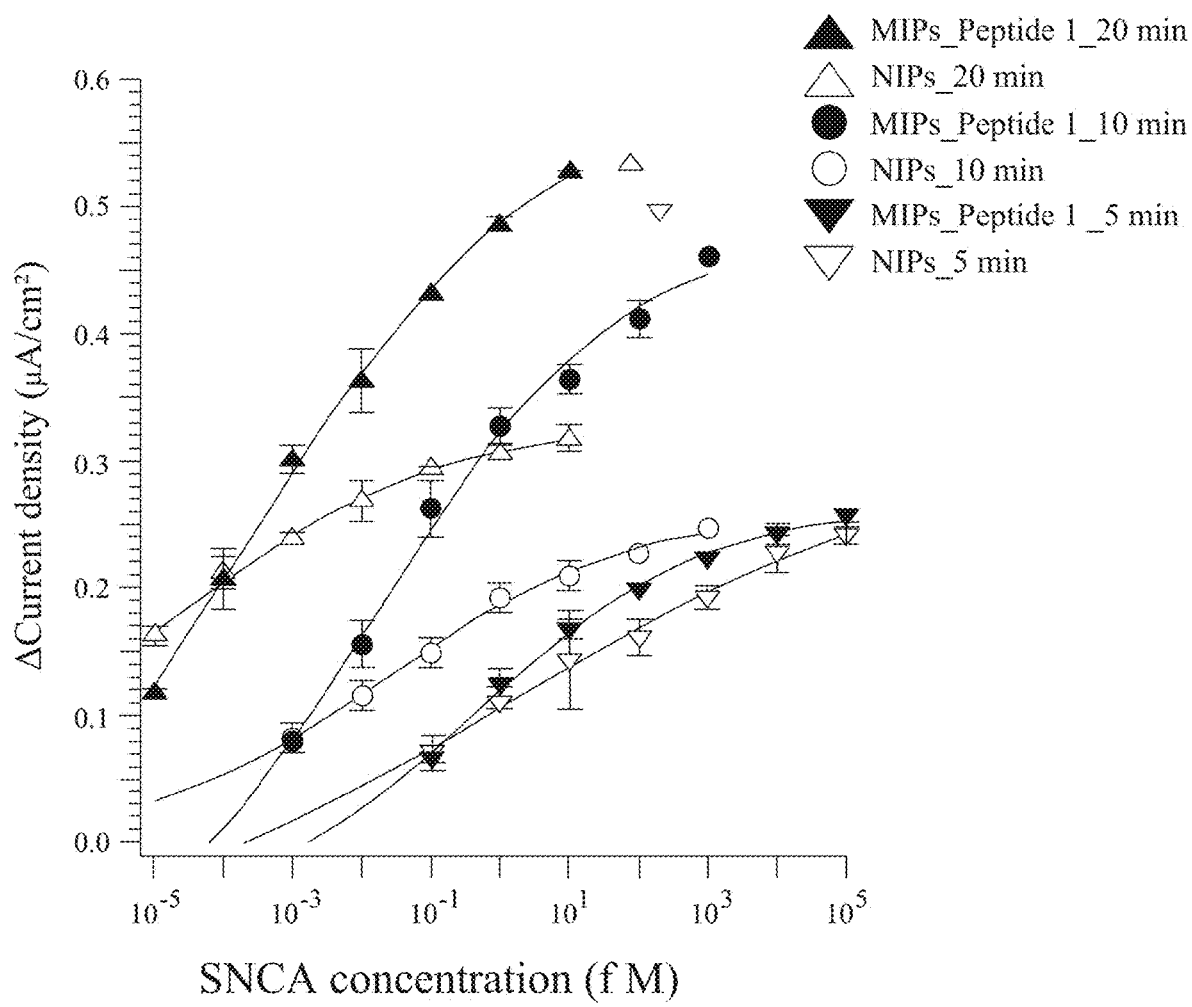
FIG. 16 is a line graph showing a current density differences of an α-synuclein sensing film of the present invention interacting to a first α-synuclein peptide.

The MIPs_EDOT-OH_Peptide 1 and the NIPs_EDOT-OH are respectively reacting with α-synuclein for 5 minutes, 10 minutes and 20 minutes, and the Δcurrent density of the MIPs_EDOT-OH_Peptide 1 and the NIPs_EDOT-OH are analyzed. Referring to FIG. 16, the current density differences of the MIPs_EDOT-OH_Peptide 1 reacting for 20 minutes is the highest and is significantly different from the current density differences of the NIPs_EDOT-OH reacting for 20 minutes. The current density differences of the MIPs_EDOT-OH_Peptide 1 reacting for 10 minutes is middle and is also significantly different from the current density differences of the NIPs_EDOT-OH reacting for 10 minutes. The current density differences of the MIPs_EDOT-OH_Peptide 1 reacting for 5 minutes is the lowest and is not significantly different from the current density differences of the NIPs_EDOT-OH reacting for 5 minutes.

Figure 17:
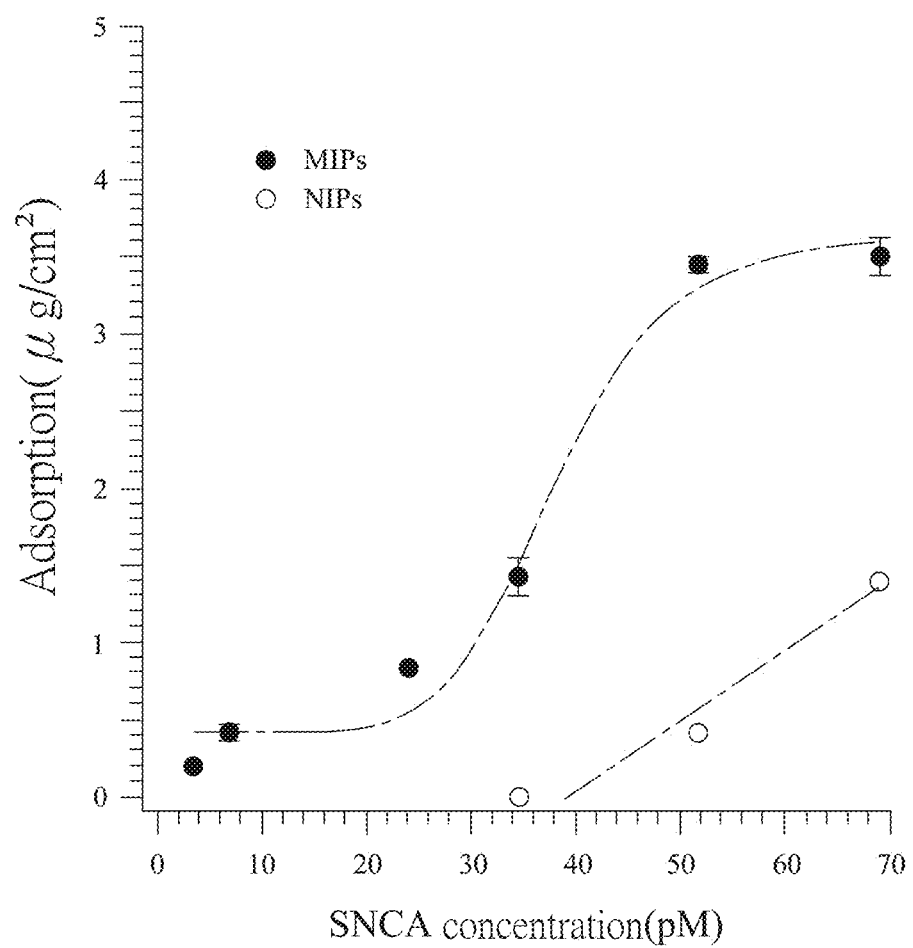
FIG. 17 is a line graph showing an adsorption ability to α-synuclein of an α-synuclein sensing film of the present invention.

Referring to FIG. 17, the MIPs_EDOT-OH_Peptide 1 and the NIPs_EDOT-OH are first reacting with different concentration of α-synuclein (SNCA), and the SNCA on the MIPs_EDOT-OH_Peptide 1 and the NIPs_EDOT-OH are then analyzed by enzyme-linked immunosorbent assay (ELISA). According to FIG. 17, the maximum binding capacity to α-synuclein of the MIPs_EDOT-OH_Peptide 1 is 3.65 μg/cm$^2$.

Figure 18A:
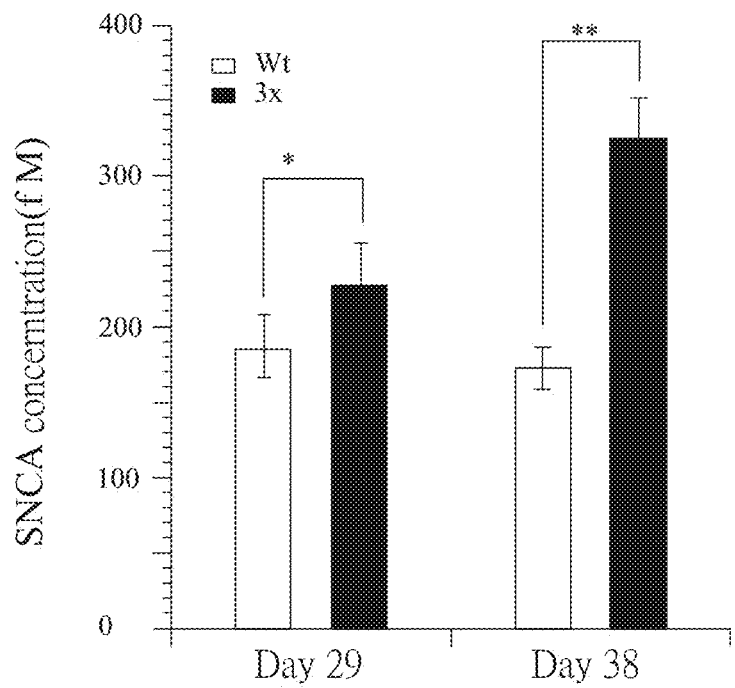
FIG. 18 (A) is a bar chart showing detection of SNCA in a cultured medium of midbrain organoids by an α-synuclein sensing film of the present invention.
Figure 18B:
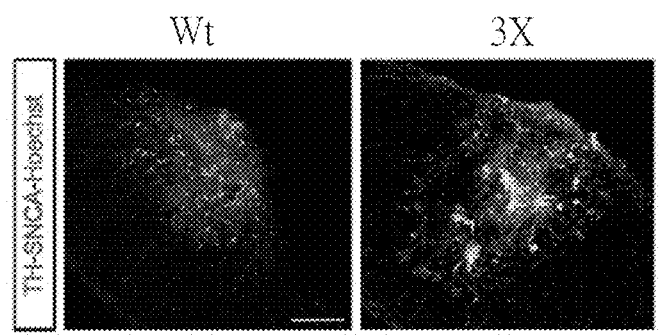

Further, two ventralized neural epithelial stein cell lines (vNESCs) were induced from two induced pluripotent stein cell lines (iPSC), and the two ventralized neural epithelial stein cell lines are further developed to midbrain organoids. One of the vNESCs has a wild-type α-synuclein gene (aligned as "wt" in FIG. 18), and the other vNESCs has a triplication in the α-synuclein gene (aligned as "3×" in FIG. 18). The midbrain organoids are incubated in a medium and the medium is replaces every 3 days. At day 29 and day 38 after incubation, the culture medium is collected and analyzed by the MIPs_EDOT-OH_Peptide 1 of the present invention. Referring to FIG. 18, the SCNA concentration in the culture medium of the wt group is 186.7 (±11.1%) fM, and the SCNA concentration of the 3× group is 228.2 (±12.1%) fM at Day 29. At day 38, the SCNA concentration in the culture medium of the wt group is 182.9 (±8.0%) fM, and the SCNA concentration of the 3× group is 325.0 (±8.5%) fM. It suggested that the 3× midbrain organoid produces higher amount of SCNA than the wt midbrain organoid. The midbrain organoids are further analyzed by immunofluorescence assay. Referring to FIG. 18(B), the SCNA in the midbrain organoid is stained by anti-SCNA antibody and presented as a red color. According to FIG. 18(B), SCNA is rarely detected in the wt midbrain organoid. However, in the 3× midbrain organoid, a lot of SCNA is detected.

Accordingly, the α-synuclein sensing film of the present invention can be used to detect α-synuclein content in many kinds of samples including but not limited to a blood sample, an urine sample, a saliva sample, a cerebrospinal sample or a sample extraction from a tissue or an organ. Therefore, the α-synuclein sensing film of the present invention is convenient to use and has high accuracy.

What is claimed is:

1. An α-synuclein sensing film, comprising a base plate and a plurality of α-synuclein sensing polymers polymerized on the base plate, wherein each of the plurality of α-synuclein sensing polymers has a plurality of a-synuclein detection holes on a surface thereof, wherein the plurality of a-synuclein sensing polymers are high molecular weight polymers imprinted by an α-synuclein peptide, and wherein an amino acid sequence of the α-synuclein peptide is selected from the group consisting of SEQ ID NO:1, SEQ ID NO:2, SEQ ID NO:3 and SEQ ID NO:4.

2. The α-synuclein sensing film as claimed in claim 1, wherein the base plate is a conductive base plate.

3. The α-synuclein sensing film as claimed in claim 2, wherein the conductive base plate is an indium tin oxide base plate, and wherein the high molecular weight polymers are polymerized by 3,4-ethylenefioxythiophene, hydroxymethyl 3,4-ethylenedioxythiophene or a combination thereof.

4. The α-synuclein sensing film as claimed in claim 1, having a current density ranging from 0.01 to 500 mA.

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 1

Tyr Val Gly Ser Lys Thr Lys Glu Gly Val Val His Gly Val Ala
1               5                   10                  15

<210> SEQ ID NO 2
<211> LENGTH: 15
<212> TYPE: PRT
<213> ORGANISM: Homo sapiens
<220> FEATURE:
<223> OTHER INFORMATION: SYNTHETIC PEPTIDE

<400> SEQUENCE: 2

Tyr Val Gly Ser Lys Thr Lys Glu Gly Val Val His Gly Val Thr
1               5                   10                  15
```

```
<210> SEQ ID NO 3
<211> LENGTH: 15
<212> TYPE: PRT
<213> ORGANISM: Homo sapiens
<220> FEATURE:
<223> OTHER INFORMATION: SYNTHETIC PEPTIDE

<400> SEQUENCE: 3

Tyr Val Gly Ser Lys Thr Lys Gly Val Val His Gly Val Thr
1               5                   10                  15

<210> SEQ ID NO 4
<211> LENGTH: 13
<212> TYPE: PRT
<213> ORGANISM: Homo sapiens
<220> FEATURE:
<223> OTHER INFORMATION: SYNTHETIC PEPTIDE

<400> SEQUENCE: 4

Ala Glu Ala Ala Gly Lys Thr Lys Glu Gly Val Leu Thr
1               5                   10
```